US006808701B2

(12) United States Patent
Duden et al.

(10) Patent No.: US 6,808,701 B2
(45) Date of Patent: Oct. 26, 2004

(54) CONDITIONING COMPOSITIONS

(75) Inventors: Carol A. Duden, Lambertville, NJ (US); Daniel Donnelly, East Brunswick, NJ (US); Geoffrey Trivino, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 116 days.

(21) Appl. No.: 09/804,810

(22) Filed: Mar. 13, 2001

(65) Prior Publication Data

US 2001/0051142 A1 Dec. 13, 2001

Related U.S. Application Data

(60) Provisional application No. 60/190,814, filed on Mar. 21, 2000.

(51) Int. Cl.$^7$ ............................................. A61K 7/075
(52) U.S. Cl. .................. 424/70.19; 424/70.11; 424/70.21; 424/70.22; 424/70.23; 424/70.24; 424/70.27; 424/70.28; 424/70.31; 424/401
(58) Field of Search ................. 424/70.11, 70.19, 424/70.21, 70.22, 70.23, 70.24, 70.27, 70.28, 703, 401

(56) References Cited

U.S. PATENT DOCUMENTS

| | | | |
|---|---|---|---|
| 4,185,087 A | 1/1980 | Morlino ........................ 424/70 |
| 4,243,657 A | 1/1981 | Okumura et al. ............. 424/47 |
| 4,337,166 A | 6/1982 | Hill et al. ............... 252/174.15 |
| 4,364,837 A | 12/1982 | Pader ......................... 252/173 |
| 4,372,869 A | 2/1983 | Lindemann et al. ... 252/174.16 |
| 4,374,825 A | 2/1983 | Bolich, Jr. et al. ............. 424/70 |
| 4,380,637 A | 4/1983 | Lindemann et al. ........ 548/112 |
| 4,382,036 A | 5/1983 | Lindemann et al. ........ 260/403 |
| 4,387,090 A | 6/1983 | Bolich, Jr. ..................... 424/70 |
| 4,421,769 A | 12/1983 | Dixon et al. ................. 424/358 |
| 4,450,152 A | 5/1984 | Ona et al. ...................... 424/70 |
| 4,472,375 A | 9/1984 | Bolich, Jr. et al. ............. 424/70 |
| 4,479,893 A | 10/1984 | Hirota et al. ................. 252/542 |
| 4,486,333 A | 12/1984 | Sebba ......................... 252/307 |
| 4,529,586 A | 7/1985 | De Marco et al. ............. 424/70 |
| 4,559,227 A | 12/1985 | Chandra et al. ............... 424/70 |
| 4,563,347 A | 1/1986 | Starch ........................... 424/70 |
| 4,567,038 A | 1/1986 | Ciaudelli et al. ............... 424/59 |
| 4,568,667 A * | 2/1986 | Shirakawa et al. |
| 4,597,962 A | 7/1986 | Grollier et al. ................ 424/47 |
| 4,597,964 A | 7/1986 | Ziemelis et al. ............... 424/70 |
| 4,617,414 A | 10/1986 | Lukenbach et al. ........... 558/87 |
| 4,654,161 A | 3/1987 | Kollmeier et al. ..... 252/174.15 |
| 4,673,568 A | 6/1987 | Grollier et al. ................ 424/47 |
| 4,704,272 A | 11/1987 | Oh et al. ....................... 424/70 |
| 4,710,314 A | 12/1987 | Madrange et al. ........... 252/117 |
| 4,728,457 A | 3/1988 | Fieler et al. ........... 252/174.15 |
| 4,741,855 A | 5/1988 | Grote et al. ................. 252/142 |
| 4,749,565 A | 6/1988 | Grollier ........................ 424/70 |
| 4,749,732 A | 6/1988 | Kohl et al. .................... 524/43 |
| 4,777,037 A | 10/1988 | Wagman et al. ............... 424/70 |
| 4,788,006 A | 11/1988 | Bolich, Jr. et al. .......... 252/550 |
| 4,818,523 A | 4/1989 | Clarke et al. .................. 424/70 |
| 4,839,167 A | 6/1989 | Yamamoto et al. ........... 424/71 |
| 4,842,850 A | 6/1989 | Vu ............................... 424/70 |
| 4,847,071 A * | 7/1989 | Bissett et al. |
| 4,902,499 A | 2/1990 | Bolish, Jr. et al. ............. 424/70 |
| 4,906,459 A | 3/1990 | Cobb et al. .................... 424/70 |
| 4,910,013 A | 3/1990 | Kanamaru et al. ............ 424/47 |
| 4,915,938 A | 4/1990 | Zawadzki ..................... 424/70 |
| 4,933,176 A | 6/1990 | van Reeth .................... 424/70 |
| 4,954,335 A | 9/1990 | Janchipraponvej ........... 424/70 |
| 4,973,476 A | 11/1990 | Krzysik ........................ 424/71 |
| 4,976,956 A | 12/1990 | Noe .............................. 424/70 |
| 4,983,383 A | 1/1991 | Maksimoski et al. ......... 424/70 |
| 4,997,641 A | 3/1991 | Hartnett et al. ............... 424/70 |
| 5,034,218 A | 7/1991 | Duvel .......................... 424/70 |
| 5,049,377 A | 9/1991 | Lamb et al. ................... 424/70 |
| 5,063,044 A | 11/1991 | Kohl et al. .................... 424/70 |
| 5,063,052 A | 11/1991 | Grollier et al. ................ 424/70 |
| 5,077,041 A | 12/1991 | Yamashina et al. ........... 424/70 |
| 5,078,990 A | 1/1992 | Martin et al. ................. 424/70 |
| 5,085,857 A | 2/1992 | Reid et al. .................... 424/70 |
| 5,093,109 A * | 3/1992 | Mausner |
| 5,100,657 A | 3/1992 | Ansher-Jackson et al. .... 424/70 |
| 5,106,609 A | 4/1992 | Bolich, Jr. et al. ............. 424/70 |
| 5,106,613 A | 4/1992 | Hartnett et al. ............... 424/71 |
| 5,114,706 A | 5/1992 | Duvel .......................... 424/70 |
| 5,120,531 A | 6/1992 | Wells et al. ................... 424/70 |
| 5,151,210 A | 9/1992 | Steuri et al. ........... 252/174.017 |
| 5,152,914 A | 10/1992 | Forster et al. ............. 252/174 |
| 5,160,449 A | 11/1992 | Halloran ................ 252/174.15 |
| 5,160,733 A | 11/1992 | Berthiaume et al. .......... 424/71 |
| 5,169,623 A | 12/1992 | Kopolow et al. .............. 424/47 |

(List continued on next page.)

FOREIGN PATENT DOCUMENTS

| | | |
|---|---|---|
| AU | 607174 B | 2/1991 |
| AU | 47580/93 A1 | 3/1994 |
| AU | 654850 B | 11/1994 |
| AU | 664987 B | 12/1995 |
| AU | 668546 B | 5/1996 |
| AU | 701232 B2 | 1/1999 |

(List continued on next page.)

OTHER PUBLICATIONS

Information About *Dow Corning*® 2–5324 Fluid, 1997, 4 pages.

Information About *Dow Corning*® 190 and 193 Surfactants, 1997, 2 pages.

*Primary Examiner*—Jyothsna Venkat

(57) ABSTRACT

A conditioning composition comprised of a mixture of anionic, amphoteric, and nonionic surfactants, branched quaternary polymers, and silicone which imparts cleansing, wet detangling, dry detangling and manageability to hair and which is relatively non-irritating and thus suitable for use by young children and adults having sensitive skin and eyes. The conditioning composition is able to provide such benefits in an aesthetically pleasing formulation without the need for suspending agents, opacifiers, or pearlizing agents.

23 Claims, No Drawings

U.S. PATENT DOCUMENTS

| | | | |
|---|---|---|---|
| 5,180,584 A | 1/1993 | Sebag et al. | 424/401 |
| 5,196,187 A | 3/1993 | Nicoll et al. | 424/70 |
| 5,198,209 A | 3/1993 | Zhou et al. | 424/71 |
| 5,213,716 A | 5/1993 | Patel et al. | 252/547 |
| 5,217,652 A | 6/1993 | Iovanni | 252/547 |
| 5,240,695 A | 8/1993 | Dubief et al. | 424/47 |
| 5,246,694 A | 9/1993 | Birthwistle | 424/70 |
| 5,248,445 A | 9/1993 | Rizvi et al. | 252/174.15 |
| 5,252,324 A | 10/1993 | Bires et al. | 424/70 |
| 5,260,055 A | 11/1993 | Imperante et al. | 424/71 |
| 5,262,325 A | 11/1993 | Zimmermann et al. | 435/269 |
| 5,275,761 A | 1/1994 | Bergmann | 252/551 |
| 5,290,545 A | 3/1994 | Halloran et al. | 424/70 |
| RE34,584 E | 4/1994 | Grote et al. | 252/142 |
| 5,306,434 A | 4/1994 | Schueller et al. | 252/8.8 |
| 5,308,551 A | 5/1994 | Beauquey et al. | 252/548 |
| 5,328,685 A | 7/1994 | Janchitraponvej et al. | 424/71 |
| 5,332,569 A | 7/1994 | Wood et al. | 424/70 |
| 5,334,376 A | 8/1994 | Robbins et al. | 424/70 |
| 5,346,642 A | 9/1994 | Patel et al. | 252/174.21 |
| 5,352,437 A * | 10/1994 | Nakagawa et al. | |
| 5,358,667 A | 10/1994 | Bergmann | 252/547 |
| 5,362,484 A | 11/1994 | Wood et al. | 424/70 |
| 5,362,485 A | 11/1994 | Hayama et al. | 424/70 |
| 5,374,421 A | 12/1994 | Tashiro et al. | 404/70.12 |
| 5,389,364 A | 2/1995 | Cifuentes et al. | 424/70.122 |
| 5,393,452 A | 2/1995 | Raleigh et al. | 252/174.15 |
| 5,409,628 A | 4/1995 | Heinz et al. | 252/174.17 |
| 5,409,695 A | 4/1995 | Abrutyn et al. | 424/70.12 |
| 5,417,965 A | 5/1995 | Janchitraponvej | 424/70.12 |
| 5,437,809 A | 8/1995 | Chaudhuri | 252/174.15 |
| 5,439,673 A | 8/1995 | Murray | 424/70.12 |
| 5,439,677 A | 8/1995 | Villamarin | 424/70.12 |
| 5,439,954 A | 8/1995 | Bush | 424/59 |
| 5,441,667 A | 8/1995 | Tonomura et al. | 252/174.15 |
| 5,482,703 A | 1/1996 | Pings | 454/70.12 |
| 5,536,332 A | 7/1996 | Chun | 132/202 |
| 5,536,493 A | 7/1996 | Dubief | 424/70.13 |
| 5,554,313 A | 9/1996 | Chandler | 510/121 |
| 5,556,615 A | 9/1996 | Janchitraponvej | 424/70.11 |
| 5,556,616 A | 9/1996 | Janchitraponvej et al. | 424/70.122 |
| 5,565,194 A | 10/1996 | Burkhart et al. | 424/70.12 |
| 5,573,709 A | 11/1996 | Wells | |
| 5,585,094 A | 12/1996 | Villamarin | 424/70.12 |
| 5,618,521 A * | 4/1997 | de Rigal et al. | |
| 5,618,524 A | 4/1997 | Bolich, Jr. et al. | 424/70.12 |
| 5,635,469 A * | 6/1997 | Fowler et al. | |
| 5,650,383 A | 7/1997 | Dubief et al. | 510/122 |
| 5,658,557 A | 8/1997 | Bolich, Jr. et al. | 424/70.12 |
| 5,665,337 A | 9/1997 | Carballada et al. | 424/70.12 |
| 5,667,771 A | 9/1997 | Carballada et al. | 424/70.12 |
| 5,683,685 A | 11/1997 | Hirano et al. | 424/78.03 |
| 5,710,113 A | 1/1998 | Wells | 510/122 |
| 5,720,964 A | 2/1998 | Murray | 424/401 |
| 5,723,111 A | 3/1998 | Glover et al. | 424/70.1 |
| 5,733,532 A | 3/1998 | Raspanti et al. | 424/59 |
| 5,753,216 A | 5/1998 | Leitch et al. | 424/70.12 |
| 5,756,076 A | 5/1998 | Cervantes et al. | 424/70.1 |
| 5,756,080 A | 5/1998 | Janchitraponvej et al. | 424/70.122 |
| 5,759,527 A | 6/1998 | Patel et al. | 424/70.11 |
| 5,776,443 A | 7/1998 | Vinski et al. | 424/70.12 |
| 5,776,472 A | 7/1998 | Simon et al. | 424/401 |
| 5,804,203 A * | 9/1998 | Hahn et al. | |
| 5,833,999 A | 11/1998 | Trinh et al. | 424/401 |
| 5,840,280 A | 11/1998 | Faryniarz et al. | 424/47 |
| 5,846,549 A | 12/1998 | Beauquey et al. | 424/401 |
| 5,849,310 A | 12/1998 | Trink et al. | 424/401 |
| 5,853,706 A * | 12/1998 | Klar | |
| 5,854,293 A | 12/1998 | Glenn, Jr. | 514/844 |
| 5,876,705 A | 3/1999 | Uchiyama et al. | |
| 5,879,671 A | 3/1999 | Halloran et al. | 424/70.122 |
| 5,888,488 A | 3/1999 | Fukuchi | 424/70.12 |
| 5,910,302 A | 6/1999 | Halloran et al. | 424/70.122 |
| 5,911,979 A | 6/1999 | Midha et al. | 424/70.12 |
| 5,916,547 A | 6/1999 | Torgerson et al. | 424/70.12 |
| 5,919,439 A | 7/1999 | Torgerson et al. | 424/70.122 |
| 5,932,202 A | 8/1999 | Guskey et al. | 424/70.19 |
| 5,935,560 A | 8/1999 | Seper et al. | 424/70.12 |
| 5,948,739 A | 9/1999 | Inman | 510/122 |
| 5,955,066 A | 9/1999 | Sako et al. | 424/70.12 |
| 5,965,115 A | 10/1999 | Bolich, Jr. et al. | 424/70.12 |
| 5,968,286 A | 10/1999 | Crudele et al. | 134/42 |
| 5,968,493 A | 10/1999 | Dornoff | 424/70.1 |
| 5,968,495 A | 10/1999 | Bolich, Jr. et al. | 424/70.12 |
| 5,972,356 A | 10/1999 | Peffly et al. | 424/401 |
| 5,976,517 A | 11/1999 | Dubief et al. | 424/70.1 |
| 5,977,038 A | 11/1999 | Birtwistle et al. | 510/122 |
| 5,980,876 A | 11/1999 | Peffly | 424/70.12 |
| 5,985,294 A | 11/1999 | Peffly | 424/401 |
| 5,985,297 A | 11/1999 | Mellul et al. | 424/401 |
| 5,989,532 A | 11/1999 | Haning et al. | 424/70.1 |
| 5,990,059 A | 11/1999 | Finel et al. | 510/122 |
| 5,997,853 A | 12/1999 | Bolich, Jr. et al. | 424/70.12 |
| 5,997,886 A | 12/1999 | Peffly et al. | 424/401 |
| 6,001,339 A | 12/1999 | Finel et al. | 424/70.12 |
| 6,004,540 A | 12/1999 | Richard et al. | 424/59 |
| 6,007,800 A | 12/1999 | Dubief et al. | 424/70.1 |
| 6,022,530 A | 2/2000 | Gers-Barlag et al. | 424/59 |
| 6,022,836 A | 2/2000 | Dubief et al. | 510/122 |
| 6,028,041 A | 2/2000 | Decoster et al. | 510/119 |
| 6,090,773 A * | 7/2000 | Lukenbach et al. | 510/119 |
| 6,297,203 B1 * | 10/2001 | Guskey et al. | 510/124 |
| 6,322,801 B1 * | 11/2001 | Lorenzi et al. | 424/401 |

FOREIGN PATENT DOCUMENTS

| | | |
|---|---|---|
| AU | 701962 B2 | 2/1999 |
| AU | 705326 B2 | 5/1999 |
| AU | 728490 B2 | 1/2001 |
| CA | 1261276 A1 | 9/1989 |
| CA | 1263938 A1 | 12/1989 |
| CA | 1270441 A1 | 6/1990 |
| CA | 2019352 A1 | 12/1990 |
| CA | 2071801 A1 | 12/1992 |
| CA | 2092779 A1 | 9/1993 |
| CA | 2017672 C | 12/1994 |
| CA | 2025089 C | 8/1995 |
| CA | 2180942 A1 | 8/1995 |
| CA | 2031382 C | 9/1995 |
| CA | 2009947 C | 10/1995 |
| CA | 2145474 A1 | 10/1995 |
| CA | 2161762 A1 | 6/1996 |
| CA | 2163854 A1 | 6/1996 |
| CA | 2218683 A1 | 10/1996 |
| CA | 2222059 A1 | 12/1996 |
| CA | 2234851 A1 | 4/1997 |
| CA | 2075117 C | 7/1997 |
| CA | 2098391 C | 9/1997 |
| CA | 2250384 A1 | 10/1997 |
| CA | 2250385 A1 | 10/1997 |
| CA | 2250389 A1 | 10/1997 |
| CA | 2204540 A1 | 11/1997 |
| CA | 2257188 A1 | 12/1997 |
| CA | 2261755 A1 | 2/1998 |
| CA | 2265652 A1 | 4/1998 |
| CA | 2268907 A1 | 4/1998 |
| CA | 2269762 A1 | 5/1998 |
| CA | 2271078 A1 | 5/1998 |
| CA | 2274849 A1 | 7/1998 |
| CA | 2097838 C | 8/1998 |

| | | |
|---|---|---|
| CA | 2283812 A1 | 10/1998 |
| CA | 2284595 A1 | 10/1998 |
| CA | 2300143 A1 | 2/1999 |
| CA | 2075767 C | 7/1999 |
| CA | 2164814 C | 8/1999 |
| EP | 0680743 A | 11/1995 |
| EP | 0 914 814 A1 | 5/1999 |
| EP | 0 918 069 A1 | 5/1999 |
| EP | 0 947 190 A2 | 10/1999 |
| EP | 0 951 898 A1 | 10/1999 |
| EP | 0 958 804 A2 | 11/1999 |
| EP | 0 947 190 A3 | 5/2000 |
| PH | 31167 | 3/1998 |
| WO | 94/29415 A1 | 12/1994 |
| WO | 97/03647 A1 | 2/1997 |
| WO | 9726860 A | 7/1997 |
| WO | 97/32559 A1 | 9/1997 |
| WO | 97/38673 A1 | 10/1997 |
| WO | 97/41827 A1 | 11/1997 |
| WO | 97/42935 A1 | 11/1997 |
| WO | 97/46210 A1 | 12/1997 |
| WO | 97/46211 A1 | 12/1997 |
| WO | 97/46212 A1 | 12/1997 |
| WO | 98/03155 A1 | 1/1998 |
| WO | 98/16189 A1 | 4/1998 |
| WO | 98/18434 A1 | 5/1998 |
| WO | 98/19654 A1 | 5/1998 |
| WO | 98/19655 A1 | 5/1998 |
| WO | 98/19656 A1 | 5/1998 |
| WO | 98/20833 A2 | 5/1998 |
| WO | 98/20833 A3 | 5/1998 |
| WO | 98/20845 A1 | 5/1998 |
| WO | 98/20855 A1 | 5/1998 |
| WO | 98/24408 A1 | 6/1998 |
| WO | 98/31334 A1 | 7/1998 |
| WO | 99/09939 A1 | 3/1999 |
| WO | 99/13823 A3 | 3/1999 |
| WO | 99/13823 A2 | 3/1999 |
| WO | 99/13837 A1 | 3/1999 |
| WO | 99/13839 A1 | 3/1999 |
| WO | 99/13841 A1 | 3/1999 |
| WO | 99/13842 A1 | 3/1999 |
| WO | 99/13843 A1 | 3/1999 |
| WO | 99/13846 A1 | 3/1999 |
| WO | 99/15134 A1 | 4/1999 |
| WO | 99/17719 A1 | 4/1999 |
| WO | 99/22708 A1 | 5/1999 |
| WO | 99/24004 A1 | 5/1999 |
| WO | 99/27903 A1 | 6/1999 |
| WO | 99/29286 A1 | 6/1999 |
| WO | 99/29287 A1 | 6/1999 |
| WO | 99/29291 A1 | 6/1999 |
| WO | 99/32079 A1 | 7/1999 |
| WO | 99/32539 A1 | 7/1999 |
| WO | 99/34768 A3 | 7/1999 |
| WO | 99/34768 A2 | 7/1999 |
| WO | 99/34770 A1 | 7/1999 |
| WO | 99/38476 A1 | 8/1999 |
| WO | 99/38478 A1 | 8/1999 |
| WO | 99/43289 A1 | 9/1999 |
| WO | 99/44565 A1 | 9/1999 |
| WO | 99/44567 A1 | 9/1999 |
| WO | 99/49836 A1 | 10/1999 |
| WO | 99/53889 A1 | 10/1999 |
| WO | 99/55294 A1 | 11/1999 |
| WO | 99/62466 A1 | 12/1999 |
| WO | 99/66888 A1 | 12/1999 |

* cited by examiner

CONDITIONING COMPOSITIONS

CROSS REFERENCE TO RELATED APPLICATION

This application claims priority to U.S. Provisional Application Ser. No. 60/190,814, filed Mar. 21, 2000, the disclosure of which is hereby incorporated by reference.

BACKGROUND OF THE INVENTION

1. Field of the Invention

This invention relates to conditioning detergent compositions suitable for use in personal cleansing application which not only impart cleansing, wet detangling, dry detangling and manageability properties to hair, but also which are relatively non-irritating and thus suitable for use by young children and adults having sensitive skin and eyes.

2. Description of the Prior Art

In the past, it has been considered desirable to cleanse hair and then to condition it after cleansing. For many years, it was necessary to perform these acts in two separate steps. However, with the advent of so-called "two-in-one" conditioning shampoos, it became possible to condition and cleanse simultaneously. Unfortunately, many of these two-in-one conditioning shampoos and body cleansers have proven to be relatively irritating to the eyes and skin and uncomfortable for use with children or sensitive adults. Therefore, it is an object of this invention to create a conditioning shampoo that has good cleansing ability, excellent conditioning properties and has a low degree of ocular and skin irritation.

One approach to providing hair conditioning benefits to a shampoo is described in U.S. Pat. No. 5,932,202, which discloses a composition comprised of an ethoxylated alkyl sulfate surfactant combined with an amphoteric surfactant; a cationic cellulosic polymer and a water insoluble non-volatile conditioning agent. While this shampoo claims to have optimized the conditioning properties of its cellulosic polymer by selection of a particular surfactant combination, that surfactant combination is not known as being gentle to the eyes and skin. Moreover, cationic cellulosic polymers are often disadvantageously associated with leaving an "unclean" residue to the hair and skin. Further, it is necessary to use a suspending agent for the insoluble conditioning agent in order to produce an aesthetically pleasing formulation. Typically, such formulations that required the use of a stabilizer are prone to separation and are capable of yielding only opaque products.

Alternatively, guar gum derivatives have also been employed in conditioning shampoos. U.S. Pat. No. 5,085,857 discloses compositions containing surfactants, guar gum derivatives, and insoluble, non-volatile silicones. Like the cationic cellulosic polymers, guar gum derivatives are also associated with leaving an "unclean" residue. Moreover, these compositions also require a shear thinning polymer or an insoluble solid for enhancing the composition's stability.

It would be desirable to have a conditioning composition that would not only impart cleansing, wet detangling, dry detangling and manageability properties to hair, but would also have a low degree of ocular and skin irritation. It would also be desirable to have such a conditioning composition in a clear or translucent, aesthetically pleasing formulation without the need for adding pearlizers, opacifiers, and suspending agents thereto.

SUMMARY OF THE INVENTION

In accordance with this invention, there is provided a detergent composition comprising:

a surfactant portion comprising:
1. a nonionic surfactant;
2. an amphoteric surfactant; and
3. an anionic surfactant; and a conditioner portion comprising:
1. a branched quaternary cellulosic polymer; and
2. a silicone.

Another embodiment of the present invention is directed to a conditioning detergent composition comprising, based upon the total weight of the conditioning detergent composition:

a. from about 1 percent to about 10 percent of nonionic surfactants comprising:
  1) a polyoxyethylene derivative of a polyol ester
    a. derived from a fatty acid containing from about 8 to about 22 carbon atoms and a polyol selected from sorbitol, sorbitan, glucose, α-methyl glucoside, polyglucose having an average of about 1 to about 3 glucose residues, glycerine, pentaerythritol and mixtures thereof,
    b. containing an average of from about 10 to about 120 oxyethylene units, and
    c. having an average of from about 1 to about 3 fatty acid residues per molecule of the polyoxyethylene derivative of polyol ester,
  2) an alkyl glucoside having an alkyl group containing from about 6 to about 22 carbon atoms and having from about 1 to about 6 glucose residues per molecule of alkyl glucoside, or
  3) mixtures thereof, and b. from about 0.5 percent to about 10 percent of one or more amphocarboxylate amphoteric surfactants of the formula:

$$A\text{—}CONH(CH_2)_x N^+ R_5 R_6 R_7$$

wherein
A is an alkyl or alkenyl group having from about 7 to about 21 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or a group of the formula:

$$R_8\text{—}O\text{—}(CH_2)_n CO_2^-$$

wherein
$R_8$ is an alkylene group having from about 2 to about 3 carbon atoms and
n is 1 or 2; and
$R_7$ is a carboxyalkyl group containing from about 2 to about 3 carbon atoms, c. from about 0.5 percent to about 10 percent of one or more betaine amphoteric surfactants selected from:
  1) an alkyl betaine of the formula:

$$B\text{—}N^+ R_9 R_{10}(CH_2)_p CO_2^-$$

wherein
B is an alkyl or alkenyl group having from about 8 to about 22 carbon atoms;

$R_9$ and $R_{10}$ are each independently an alkyl group or a hydroxyalkyl group having from about 1 to about 4 carbon atoms; and p is 1 or 2; or 2) an amidoalkyl betaine of the formula:

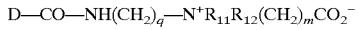

wherein

D is an alkyl or alkenyl group having from about 7 to about 21 carbon atoms;

$R_{11}$ and $R_{12}$ are each independently an alkyl group or a hydroxyalkyl group having from about 1 to about 4 carbon atoms;

q is an integer from about 2 to about 6; and m is 1 or 2;

d. from about 1 percent to about 10 percent of one or more anionic alkyl ether sulfate surfactants of the formula

wherein

R' is an alkyl or alkenyl group having from about 7 to about 22 carbon atoms,

X' is selected from the group consisting of alkali metal ions, alkaline earth metal ions, ammonium ions, ammonium ions substituted with from 1 to 3 substituents, each of the substituents may be the same or different and are selected from alkyl groups having from about 1 to about 4 carbon atoms and hydroxyalkyl groups having from about 2 to about 4 carbon atoms, and v is an integer from 1 to 6;

e. from about 0.001 percent to about 5.0 percent of polyquaternium 44; and f. from about 0.01 percent to about 8.0 percent of silicone; wherein the surfactants in a through d are present in an amount, based upon the total weight of the detergent composition, from about 5 percent to about 20 percent.

Another embodiment is directed to a method for making an aesthetically pleasing conditioning detergent composition in the substantial absence of suspending agents, opacifiers, and pearlizers comprising:

a) adding an effective amount of a branched quaternary cationic polymer to at least one surfactant.

Yet another embodiment is directed to a conditioning composition comprised of a) at least one surfactant selected from the group consisting of anionic surfactants, non-ionic surfactants, amphoteric surfactants, zwitterionic surfactants, cationic surfactants, betaine surfactants, and mixtures thereof, and b) a conditioning portion comprised of
1) a branched quaternary cationic polymer containing polyquaternium 44; and
2) a silicone.

The composition of this invention, when used in a shampoo or body cleanser, possesses superior conditioning properties as well as one or more of the following properties: cleansing, shine, low dry static, softness, wet detangling, dry detangling, manageability, and low degree of ocular irritation. In addition, the composition may be made into various, aesthetically pleasing consumer cleansing products without the need for pearlizers, suspending agents or opacifiers.

DETAILED DESCRIPTION OF PREFERRED EMBODIMENTS

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

In one embodiment of the present invention, the conditioning composition may suitably comprise, consist of, or consist essentially of a surfactant portion comprising, consisting of, or consisting essentially of an anionic surfactant, an amphoteric surfactant, and a non-ionic surfactant; and a conditioning portion comprising, consisting of, or consisting essentially of a branched quaternary conditioning polymer and a silicone.

The conditioning composition is preferably comprised of, based upon the total weight of the conditioning composition, from about 5 percent to about 20 percent, and more preferably from about 10 percent to about 15 percent of a surfactant portion and from about 0.1 percent to about 6 percent, preferably from about 0.5 percent to about 4 percent, and more preferably from about 1 percent to about 3 percent, of a conditioner portion.

In this embodiment, the surfactant portion of the present invention contains nonionic, amphoteric and anionic surfactants. Preferably the weight ratio between the amphoteric surfactant and the anionic surfactant may range from about 3:1 to about 1:3, and preferably from about 2:1 to about 1:2. The weight ratio of the amphoteric/anionic surfactant combination:non-ionic surfactant may vary widely, and preferably is about 2:1 to about 1:2. The nonionic surfactant is present in an amount, based upon the total weight of the shampoo composition, of from about 0.1 percent to about 10 percent, preferably from about 1 percent to about 10 percent, and more preferably from about 4 percent to about 8 percent. The amphoteric surfactant is present in an amount, based upon the total weight of the shampoo composition, of from about 0.5 percent to about 10 percent, preferably from about 1 percent to about 8 percent, and more preferably from about 2 percent to about 6 percent. The anionic surfactant is present in the shampoo composition in an amount from about 1.0 percent to about 10 percent, preferably from about 1 percent to about 8 percent, and more preferably from about 1 percent to about 6 percent, based on the overall weight of the shampoo composition.

One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerin, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del.

under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. The alkyl gluocosides have about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

The compositions of the present invention also contain an amphoteric surfactant. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Commercially available amphoteric surfactants are suitable for use in the present invention and include, but are not limited to amphocarboxylates, alkyl betaines, amidoalkyl betaines, amidoalkyl sultaines, amphophosphates, phosphobetaines, pyrophosphobetaines, carboxyalkyl alkyl polyamines and mixtures thereof.

Examples of suitable amphocarboxylate compounds include those of the formula:

wherein

A is an alkyl or alkenyl group having from about 7 to about 21, and preferably from about 10 to about 16 carbon atoms;

x is an integer of from about 2 to about 6;

$R_5$ is hydrogen or a carboxyalkyl group containing from about 2 to about 3 carbon atoms, and preferably is hydrogen;

$R_6$ is a hydroxyalkyl group containing from about 2 to about 3 carbon atoms or is a group of the formula:

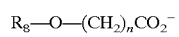

wherein $R_8$ is an alkylene group having from about 2 to about 3 carbon atoms and n is 1 or 2; and $R_7$ is a carboxyalkyl group containing from about 2 to about 3 carbon atoms;

Preferably, the amphocarboxylate compound is an imidazoline surfactant, and more preferably a disodium lauroamphodiacetate, which is commercially available from Mona Chemical Company of Paterson, N.J. under the tradename, "Monateric 949J." When an amphocarboxylate is used in the shampoo composition, it should be present in an amount of about 0.5 percent to about 10 percent, and preferably from about 0.5 percent to about 6 percent, based on the overall weight of the composition.

Examples of suitable alkyl betaines include those compounds of the formula:

wherein

B is an alkyl or alkenyl group having from about 8 to about 22, and preferably from about 8 to about 16 carbon atoms;

$R_9$ and $R_{10}$ are each independently an alkyl or hydroxyalkyl group having from about 1 to about 4 carbon atoms; and p is 1 or 2.

A preferred betaine for use in the present invention is lauryl betaine, available commercially from Albright & Wilson, Ltd. of West Midlands, United Kingdom as "Empigen BB/J." If present, the alkyl betaine should be used in an amount, based on the overall weight of the composition, of from about 0.25 percent to about 10 percent, preferably from about 0.25 percent to about 8 percent, and more preferably, from about 0.25 percent to about 5 percent.

Examples of suitable amidoalkyl betaines include those compounds of the formula:

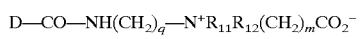

wherein

D is an alkyl or alkenyl group having from about 7 to about 21, and preferably from about 7 to about 15 carbon atoms;

$R_{11}$ and $R_{12}$ are each independently an alkyl or hydroxyalkyl group having from about 1 to about 4 carbon atoms;

q is an integer from about 2 to about 6; and m is 1 or 2.

A preferred amidoalkyl betaine is cocamidopropyl betaine, available commercially from Goldschmidt Chemical Corporation of Hopewell, Va. under the tradename, "Tegobetaine L7." When present in the shampoo compositions of this invention, the amidoalkyl betaine should be used in an amount of from about 0.25 percent to about 10 percent, preferably from about 0.25 percent to about 8 percent, and more preferably from about 0.25 percent to about 5 percent, based on the overall weight of the composition.

Examples of suitable amidoalkyl sultaines include those compounds of the formula

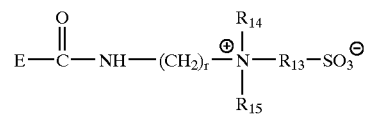

wherein

E is an alkyl or alkenyl group having from about 7 to about 21, and preferably from about 7 to about 15 carbon atoms;

$R_{14}$ and $R_{15}$ are each independently an alkyl, or hydroxyalkyl group having from about 1 to about 4 carbon atoms;

r is an integer from about 2 to about 6; and $R_{13}$ is an alkylene or hydroxyalkylene group having from about 2 to about 3 carbon atoms;

Preferably the amidoalkyl sultaine is cocamidopropyl hydroxysultaine, available commercially from Rhone-Poulenc Inc. of Cranbury, N.J. under the tradename, "Mirataine CBS." When present in the shampoo compositions of this invention, it should be used in an amount of from about 0.5 percent to about 10 percent, preferably from about 1.0 percent to about 6 percent, and more preferably from about 1.5 percent to about 5 percent, based on the overall weight of the composition.

Examples of suitable amphophosphate compounds include those of the formula:

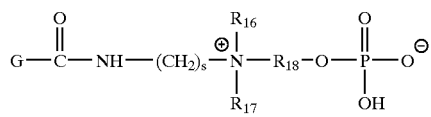

wherein
G is an alkyl or alkenyl group having about 7 to about 21, and preferably from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

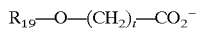

wherein
$R_{19}$ is an alkylene or hydroxyalkylene group having from about 2 to about 3 carbon atoms and
t is 1 or 2; and
$R_{18}$ is an alkylene or hydroxyalkylene group having from about 2 to about 3 carbon atoms.

Preferably the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference, with sodium lauroampho PG-acetate phosphate being most preferred.

Examples of suitable phosphobetaines include those compounds of the formula:

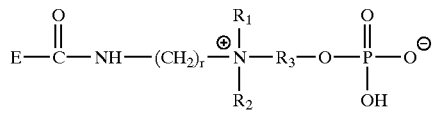

wherein E, r, $R_1$, $R_2$ and $R_3$, are as defined above. Preferably the phosphobetaine compounds are those disclosed in U.S. Pat. Nos. 4,215,064, 4,617,414, and 4,233,192.

Examples of suitable pyrophosphobetaines include those compounds of the formula:

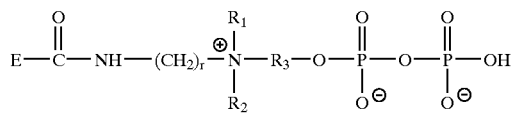

wherein E, r, $R_1$, $R_2$ and $R_3$, are as defined above. Preferably the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

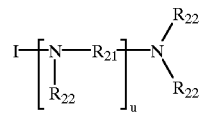

wherein
I is an alkyl or alkenyl group containing from about 8 to about 22, and preferably from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Preferably the carboxyalkyl alkyl polyamine is sodium carboxymethyl coco polypropylamine, available commercially from Akzo Nobel Surface Chemistry under the tradename, "Ampholak 7CX/C." When present in the shampoo compositions of this invention, it should be used in an amount of from about 0.5 percent to about 10 percent, preferably from about 1.0 percent to about 8 percent, and more preferably from about 2.0 percent to about 6.0 percent, based on the overall weight of the composition.

In a preferred embodiment, the amphoteric surfactant portion of the conditioning composition is comprised of a mixture of amphoteric surfactants, such as amphocarboxylate and alkyl betaine, or amphocarboxylate and amidoalkyl betaine. In this embodiment, the amphocarboxylate is present in the conditioning composition in an amount, based upon the total weight of the conditioning composition, of from about 0.5 percent to about 9.5 percent and the alkyl betaine or amidoalkyl betaine is present in an amount, based upon the total weight of the shampoo composition, of from about 9.5 percent to about 0.5 percent.

The conditioning compositions of this embodiment also contain at least ONE anionic surfactant. Preferably, the anionic surfactant is selected from the following classes of surfactants:

an alkyl sulfate of the formula

an alkyl ether sulfate of the formula

an alkyl monoglyceryl ether sulfate of the formula

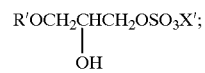

an alkyl monoglyceride sulfate of the formula

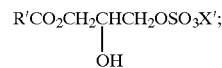

an alkyl monoglyceride sulfonate of the formula

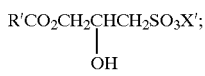

an alkyl sulfonate of the formula

an alkylaryl sulfonate of the formula

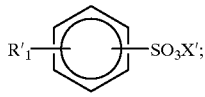

an alkyl sulfosuccinate of the formula:

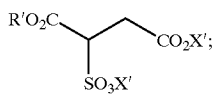

an alkyl ether sulfosuccinate of the formula:

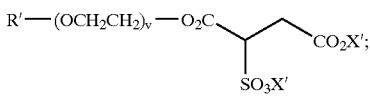

an alkyl sulfosuccinamate of the formula:

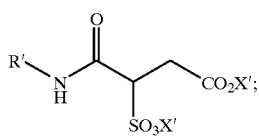

an alkyl amidosulfosuccinate of the formula

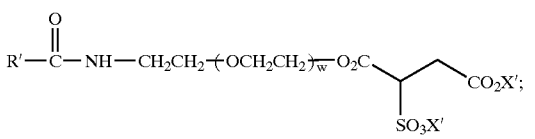

an alkyl carboxylate of the formula:

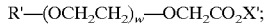

an alkyl amidoethercarboxylate of the formula:

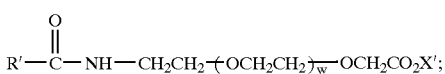

an alkyl succinate of the formula:

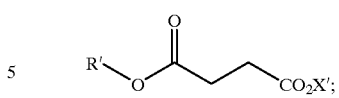

a fatty acyl sarcosinate of the formula:

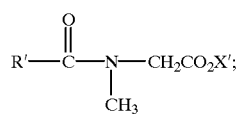

a fatty acyl amino acid of the formula:

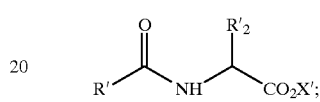

a fatty acyl taurate of the formula:

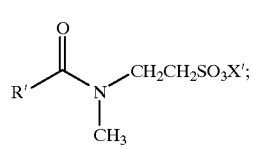

a fatty alkyl sulfoacetate of the formula:

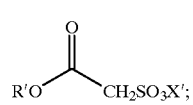

an alkyl phosphate of the formula:

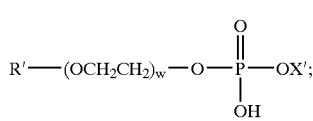

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic α-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof. Preferably the anionic surfactant is comprised of sodium trideceth sulfate, sodium laureth sulfate, disodium laureth sulfosuccinate, or mixtures thereof. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M." Sodium laureth sulfate is available from Albright & Wilson, Ltd. West Midlands, United Kingdom under the tradename, "Empicol 0251/70-J." Disodium laureth sulfosuccinate is available commercially from Albright & Wilson, Ltd. of West Midlands, United Kingdom under the tradename, "Empicol SDD."

In a preferred embodiment, the conditioning compositions of the present invention contain a surfactant portion comprised of, based upon the total weight of the conditioning composition, from about 1 percent to about 5 percent sodium trideceth sulfate; from about 2 percent to about 6 percent cocamidopropyl betaine; from about 1 percent to about 5 percent lauroamphodiacetate; and from about 3 percent to about 8 percent of PEG 80 sorbitan laurate.

In this embodiment, the shampoo composition of the present invention also contains a conditioner portion which is comprised of the following conditioning components:
1. branched quaternary cationic polymers; and
2. silicones.

The amount of branched quaternary cationic polymer conditioner component may range, based upon the total weight of the conditioning composition, from about 0.001 percent to about 5.0 percent, preferably from about 0.01 percent to about 3.0 percent, and more preferably from about 0.1 to about 1.0 percent.

The amount of silicone conditioner component may range, based upon the total weight of the conditioning composition, from about 0.01 percent to about 8.0 percent, preferably from about 0.1 percent to about 5.0 percent, and more preferably from about 0.2 to about 3.0 percent.

The amount of branched quaternary cationic polymer conditioner component may range, based upon the total weight of the conditioning portion of the conditioning composition, from about 6 percent to about 25 percent, preferably from about 10 percent to about 22 percent, and more preferably from about 15 to about 20 percent.

In one embodiment, the conditioning portion contains a quaternary cationic polymer: silicone conditioner combination in a weight ratio of from about 1:4 to about 1:6.

Preferred branched quaternary cationic polymer conditioners include the vinylpyrrolidone/vinylimidazolium copolymers. Preferred vinylpyrrolidone/vinylimidazolium copolymers include the materials known as Polyquaternium-44, which is a vinylpyrrolidone/vinylimidazolium methosulfate copolymer that is commercially available from BASF Corporation under the tradename, "Luviquat Care MF370;" Polyquaternium 16, which is a vinylpyrrolidone/vinylimidazolium methyl chloride copolymer that is commercially available from BASF Corporation under the tradename, "Luviquat FC905;" and mixtures thereof, with Polyquaternium-44 being preferred.

Preferred branched quaternary cationic polymers have a molecular weight of greater than about 100,000 and a cationic charge density of about 1.0 meq/gram to about 6.5 meq/gram.

In embodiments using a mixture of the branched quaternary cationic polymers, the Polyquaternium 44 and Polyquaternium 16 may be used in amounts, based upon the total weight of the branched quaternary cationic polymers, from about 70 percent to about 90 percent, and preferably from about 75 percent to about 85 percent of Polyquaternium 44 and from about 10 percent to about 30 percent, and preferably from about 15 percent to about 25 percent of Polyquaternium 16.

Examples of suitable silicones include volatile silicones, non-volatile silicones, and mixtures thereof, with the non-volatile silicones being preferred. The silicones may be water soluble, water insoluble, or mixtures thereof with the latter being preferred. Examples of suitable water insoluble silicones include, for e.g., those set forth in U.S. Pat. No. 5,932,202. Examples of water soluble silicones include, for e.g., dimethicone copolyol.

Preferred volatile silicone conditioning agents have an atmospheric pressure boiling point less than about 220° C. Examples of suitable volatile silicones nonexclusively include trimethylsilylamodimethicone, phenyl trimethicone, polydimethylsiloxane having a viscosity less than about 5 cSt, polydimethylcyclosiloxanes, hexamethyidisiloxane, cyclomethicone fluids such as such as those available commercially from Dow Corning Corporation of Midland, Mich. under the tradename, "DC-345" and mixtures thereof.

Examples of suitable nonvolatile silicone conditioning agents nonexclusively include organo-substituted polysiloxanes, which are either linear or cyclic polymers of monomeric silicone/oxygen monomers and which nonexclusively include cetyl dimethicone; cetyl triethylammonium dimethicone copolyol phthalate; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone and mixtures thereof; polyaryl siloxanes such as phenyl trimethicone; polyalkyl siloxanes such as the amino substituted amodimethicones; polyalkylarylsiloxanes; and derivatives there of and mixtures thereof.

The non-volatile silicone agents preferably have a viscosity of from about 10 to about 5000 centistokes, and more preferably from about 50 centistokes to about 3000 centistokes at 25° C. The viscosity can be measured by using a glass capillary viscometer as set forth in Dow Corning Corporate Test Method CTM0004 of Jul. 20, 1970.

In a preferred embodiment, the silicone conditioning agent is comprised of at least trimethylsilylamodimethicone and/or dimethicone copolyol, in an amount, based upon the total weight of the silicone conditioning agent, from about 40 percent to about 60 percent, and preferably from about 45 percent to about 55 percent trimethylsilylamodimethicone and from about 60 percent to about 40 percent, and preferably from about 55 percent to about 45 percent dimethicone copolyol.

Preferably, the conditioning composition of the present invention may be manufactured in the substantial absence of pearlizing agents, opacifiers, or suspending agents. By "substantial absence," it is meant that the conditioning compositions contains, based upon the total weight of the conditioning composition, no more than 1.0 percent, preferably no more than 0.5 percent, and more preferably no more than 0.1 percent of a pearlizing agent, opacifier, or suspending agent. We have unexpectedly found that the conditioning composition of the present invention results in an aesthetically pleasing formulation that possesses improved detangling and conditioning properties in the absence of pearlizing agents, opacifiers, and suspending agents. Without wishing to be bound by theory, we believe that the resulting formulations do not phase-separate as a result of the interaction between the surfactants and the silicones with the unique structure of the branched quaternary cationic polymer. By not having to use such stabilizing agents, et al., the conditioning composition of the present invention may be colorless, clear, or translucent.

Moreover, the conditioning composition of the present invention is capable of providing such improved detangling and conditioning properties in the absence of guar-based and cellulosic-based conditioners, and thus does not leave the hair and skin with an "unclean" coating such as those associated with prior art conditioning compositions that are predominantly guar-based and/or cellulosic quaternary polymer-based.

In embodiments wherein an opaque composition may be desired, the composition of the present invention may also include one or more optional ingredients nonexclusively including a pearlescent or opacifying agent, or a thickening agent. Other optional ingredients include secondary conditioners, humectants, chelating agents, and additives which enhance their appearance, feel and fragrance, such as colorants, fragrances, preservatives, pH adjusting agents, and the like. The pH of the shampoo compositions of this invention is preferably maintained in the range of from about 5 to about 7.5, and more preferably from about 5.5 to about 7.2.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent is present in an amount, based upon the total weight of the composition, of from about 0 percent to about 3 percent, preferably from about 0.25 percent to about 2.5 percent, and more preferably, from about 0.5 percent to about 1.5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula

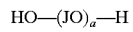

wherein
  J is an alkylene group having from about 2 to about 3 carbon atoms;
  and a is 2 or 3;
fatty alcohols containing from about 16 to about 22 carbon atoms; fatty esters of the formula

wherein K and L independently contain from about 15 to about 21 carbon atoms; inorganic solids insoluble in the shampoo composition, and mixtures thereof.
  n a preferred embodiment, the pearlescent or opacifying agent is introduced to the conditioning composition as a pre-formed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 ($CH_3(CH_2)_{10}CH_2(OCH_2CH_2)_4OH$) and cocamidopropyl betaine and preferably is in a weight percent ratio of from about 25 to about 30: about 3 to about 15: about 20 to about 25, respectively.

Commercially available thickening agents which are capable of imparting the appropriate viscosity to the conditioning shampoo compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula

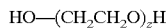

wherein z is an integer from about 3 to about 200;
and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

From about greater than 0 percent to about 4 percent, e.g. about 2 percent to about 3 percent, based upon the total weight of the conditioning composition, of commercially available secondary conditioners may optionally be added into the conditioning composition. These secondary conditioners may be comprised of from cationic cellulose derivatives; cationic guar derivatives; and a homopolymers or copolymers of a cationic monomer selected from:

a. a monomer having formula I.

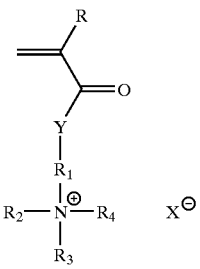

I.

wherein
    R is H or $CH_3$,
    Y is O or NH,
    $R_1$ is an alkylene group having from about 2 to about 6, and preferably from about 2 to about 3 carbon atoms,
    $R_2$, $R_3$ and $R_4$ are each independently an alkyl group having from about 1 to about 22, and preferably from about 1 to about 4 carbon atoms, and
    X is a monovalent anion selected from halide and alkyl sulfate, or
  b. diallyldimethylammonium chloride.

Examples of cationic cellulose derivatives include polymeric quaternary ammonium salts derived from the reaction of hydroxyethyl cellulose with a trimethylammonium substituted epoxide. The material known as Polyquaternium-10, commercially available from Amerchol Corporation of Edison, N.J. as "Polymer JR-400," is especially useful in this regard.

Examples of suitable cationic guar derivatives include guar hydroxypropyltrimonium chloride, available commercially from Rhone-Poulenc Inc., of Cranbury, N.J. under the tradename, "Jaguar C-17."

Another example of suitable secondary conditioners includes those compounds derived from acrylamidopropyl trimonium chloride which has the formula:

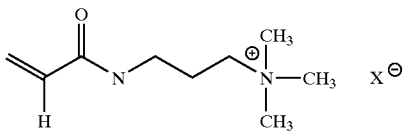

and more preferably is the copolymer of this monomer with acrylamide, the latter of which is available commercially from Allied Colloids, of Suffolk, Va. under the tradename, "Salcare SC60."

Other preferred secondary conditioners are the cationic conditioning polymers that are derived from the monomer diallyldimethylammonium chloride. The homopolymer of this monomer is Polyquaternium-6, which is available commercially from Ciba Geigy Corporation under the tradename, "Salcare SC30." The copolymer of diallyldimethylammonium chloride with acrylamide is known as Polyquaternium-7, and is also available from Ciba Geigy under the tradename "Salcare SC10."

Commercially available humectants, which are capable of providing moisturization and conditioning properties to the conditioning composition, are suitable for use in the present invention. The humectant is present in an amount of from about 0 percent to about 10 percent, preferably from about 0.5 percent to about 5 percent, and more preferably from about 0.5 percent to about 3 percent, based on the overall weight of the conditioning composition. Examples of suitable humectants nonexclusively include: 1) water soluble liquid polyols selected from the group comprising glycerin, propylene glycol, hexylene glycol, butylene glycol, dipropylene glycol, and mixtures thereof; 2) polyalkylene glycol of the formula $$HO—(R''O)_b—H$$

wherein R" is an alkylene group having from about 2 to about 3 carbon atoms and b is an integer of from about 2 to about 10;

3) polyethylene glycol ether of methyl glucose of formula $$CH_3—C_6H_{10}O_5—(OCH_2CH_2)_c—OH$$

wherein c is an integer from about 5 to about 25;

4) urea; and 5) mixtures thereof, with glycerine being the preferred humectant.

Examples of suitable chelating agents include those which are capable of protecting and preserving the compositions of this invention. Preferably, the chelating agent is EDTA, and more preferably is tetrasodium EDTA available commercially from Dow Chemical Company of Midland, Mich. under the tradename, "Versene 100XL" and is present in an amount, based upon the total weight of the composition, from about 0 to about 0.5 percent, and preferably from about 0.05 percent to about 0.25 percent. Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent, and preferably from about 0.05 percent to about 0.10 percent.

The above described conditioning composition may be prepared by combining the desired components in a suitable container and mixing them under ambient conditions in any conventional mixing means well known in the art, such as a mechanically stirred propeller, paddle, and the like. Although the order of mixing is not critical, it is preferable to pre-blend certain components, such as the fragrance and the nonionic surfactant before adding such components into the main mixture.

When a cationic guar conditioner is used, it is also preferable to preblend the cationic guar conditioner with glycerin under ambient conditions, then allow the guar conditioner to be "wet-out" by the glycerin. Although the time to "wet-out" may vary, typically this time period may range from about 5 minutes to about 30 minutes. Preferably, the guar conditioner:glycerin weight ratio is from about 1:100 to about 1:1, and more preferably from about 1:50 to about 1:5, and most preferably from about 1:15 to about 1:7. The resulting suspension is mixed with water under ambient conditions at a suspension:water weight ratio of from about 1:5 to about 1:20. The resulting water-suspension mixture is then acidified with an amount of acid, preferably citric acid, effective to reduce the pH of the overall composition to a value of about 4.

When using a thickener component, it is also preferable to preblend the desired thickener with from about 5 percent to about 20 percent, based upon the total weight of the composition, of water and preferably at a temperature of from about 60° C. to about 80° C. When processing with a thickener, it is also preferable to reduce the temperature of the overall composition to less than about 45° C. before any pre-formed pearlizer is added thereto.

The conditioning composition of the present invention is preferably used in personal cleansing applications nonexclusively including shampoos, gels such as shower gels, baths such as baby baths, washes such as body washes, and the like.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

All amounts of materials are given in parts by weight based on 100 parts of the overall formulation, unless stated otherwise. The following test procedures were used in the following Examples:

1. Half-head Study:

A girl between the ages of 7 to 11 years old wet her shoulder length hair, then parted her hair in the center in order to form two separated bunches of hair. Both bunches were secured with a hair tie. After untying one hair tie, the girl washed the released hair using a suitable amount of "Johnson's Kids No More Tangles Shampoo" available from Johnson & Johnson Consumer Companies, Inc., which contains Polyquaternium 10, polydimethylcyclosiloxane, and guar hydroxypropyltrimonium chloride. The amount of shampoo used was dependent upon the girl's respective hair type and length. The girl applied the shampoo to the released hair, then washed and rinsed that half of her head in a conventional manner. An assistant then recorded the perceived lathering, thickness, and rinsability of the girl's her hair on a scale of 1 to 5, with 5 being the highest rating.

After tying up the freshly washed hair with the hair tie, this procedure was repeated on the hair on the other side of the girl's head with an experimental formulation. The assistant then recorded the perceived lathering, thickness, and rinsability of the girl's hair relative to the same properties imparted by the commercial shampoo using the same scale.

After patting her whole head dry with a towel while ensuring that the hair on the sides of her head remained separated, an assistant combed the hair on each side of the girl's head with a wide tooth comb then evaluated the perceived wet hair attributes of wet detangling, i.e. ease of detangling the hair while wet, and wet feel, i.e., whether the rinsed hair felt clean, with residue, or dry, on the above-described scale with the exception that with respect to "wet feel", a "3" rating was superior and signified a clean feel, whereas a 1 rating signified a dry feel and a 5 signified a residue feel.

As the stylist dried the hair on one half of the girl's head, the assistant dried the hair on the other half of the girl's head using a blow dryer with similar heat and airflow patterns. The stylist then combed the hair on each side of the girl's head using the same comb in order to record the perceived dry hair attribute of dry combing. The stylist also evaluated the dry softness, dry shine, dry body, dry static, and dry feel, i.e., whether the dried hair felt clean, with residue, or dry, of the hair on each side of the girl's head using the above-described scale with the exception that with respect to "dry feel," a "3" rating was superior and signified a clean feel, whereas a 1 rating signified a dry feel and a 5 signified a residue feel.

2. Hair Conditioning Properties:

Conditioning properties of shampoos are determined by measuring the average energy and force required to comb hair in the wet and dry state after the hair has been washed with a particular shampoo formulation in accordance with the method set forth as follows:

a) Preparation of Hair samples: Human hair tresses are prepared by weighing out about 10–12 grams of virgin brown hair, and binding the cuticle end with a cable tie and hot melt glue. The cuticle end of the bundle is positioned in a binder clip. The hair is fanned out evenly over the width of the binder clip. Hot melt glue is applied along the edge of the binder clip, joining the clip and the hair. Glue is applied to the inside of the clip for further strength. A rubber band is applied to the outside of the clip, to keep the jaws of the clip from separating. The glue is allowed to dry thoroughly. The tress is washed to remove contaminants such as dust or shampoo residue by washing the tress with a non-conditioning shampoo available from The Procter and Gamble Company under the tradename, 'Original Green Prell' and allowing it to air dry. Loose hair is removed. Tangles are removed by combing the tresses with a standard comb or brush. Static charge buildup is removed using a static reducing gun.

The number of trials required for the test is equal to the number of formulations (and suitable controls) under test. The formulations are randomized such that each product is applied to each tress at some point in time. Two shampoo-ings each using about 1 cc of shampoo composition are required. The tress is thoroughly wet under running, 100° F. tap water. About 1 cc of a given shampoo composition is applied evenly from top to bottom of the tress. Using the fingers of both hands, the shampoo is rubbed into the hair for approximately 30 seconds to produce lather. The tress is then rinsed thoroughly under running, 100° F. water. The tress is then again washed and rinsed using a second 1 cc sample of product. The tress is then allowed to drip dry for 5 minutes.

The tresses are then suspended from a sturdy ring stand such that they hang freely and have several inches of clearance between the bottom of the tress and the top of the bench.

b) Wet Detangling Energy: A Combing Force Device (CFD), which is a hand held, electromechanical instrument which measures the amount of force or energy required to pass a comb through the hair, is held horizontally in the one hand and tangles are removed from the tresses by starting at the lower portion of the tress and moving the CFD downward. Each successive stroke is started at a point which is higher than the previous stroke. This measurement continues until the CFD passes freely through the entire length of the tress. Once all tangles have been removed, three top-to-bottom strokes complete the detangling measurement. The cumulative energy to detangle the hair tresses is reported as wet detangling energy, in units of gram-seconds (g/sec).

c) Wet Comb Force: After the detangling energy measurement is completed on all tresses, the tresses are measured for wet comb force. A sensor, which is attached to a curling iron having the heating element and other electronics removed therefrom, measures the twisting, or torsional force of the curling iron as the instrument is moved though the hair. The instrument is passed through the detangled tresses about 25 times. Comb force, expressed in grams, is the median force required to pass the comb through the detangled tress.

d) Dry Detangling Energy: After the tresses are blow-dried until they are no longer damp, the detangling procedure set forth in b is repeated using the dry tresses.

e) Dry Comb Force: After the tresses are blow-dried until they are no longer damp and dry detangling energy is determined, the combing procedure set forth in c) is repeated using the dry tresses.

3. Eye Irritation:

The potential for eye irritation is measured by an in vitro trans-epithelial permeability ("TEP") test. The samples are also evaluated in vivo by a human ocular irritation test.

TEP Test:

Irritation to the eyes expected for a given formulation is measured in accordance with the TEP test, as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier).

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well. A TEP score of 2.2% or higher is considered a pass, a score of 1.78% to 2.19% is considered borderline, and a score of 1.79% or below is considered a fail. The results of the test are reported in Table 7.

Human Ocular Irritation Test:

Using a double-blinded, randomized, two (2) cell study test design, one (1) drop of a sample (e.g. a 10% dilution of a cleansing composition in water) at a temperature of about 38° C. was instilled into a subject's eye. A new sterile disposable eyedropper was used for each sample and disposed of after being used on only one individual's eye. All installations were performed either by an investigator or by a trained technician.

Within 30 seconds, or as closely as possible following instillation, the subject was asked to grade the perceived stinging sensation to the eye utilizing the following criteria:

Sting
0=Within normal limits
1=Mild, very slight
2=Moderate
3=Severe

After 15 minutes and 60 minutes post-instillation, the subject was again asked to grade the perceived stinging sensation to the eye. The data was collected from a balanced, complete block experiment then statistically analyzed.

Example 1

Preparation of Conditioning Composition

The following pre-blends were prepared:

Preblend A:
1.5 parts of benzophenone 4 were mixed with 3 parts deionized water at 22° C. in a mixing vessel until a homogeneous mixture was obtained.

Preblend B:
0.1 part of dye was mixed with 10 parts of deionized water at 22° C. in a mixing vessel until a homogeneous mixture was obtained.

Preblend C:
3.5 parts of fragrance were mixed with 10 parts of PEG-80 sorbitan laurate at 22° C. in a mixing vessel until a homogeneous mixture was obtained.

Preblend D:
0.5 parts of Quaternium 15 were mixed with 1 part of deionized water at 22° C. in a mixing vessel until a homogeneous mixture was obtained.

Preblend E:
2 parts of citric acid were mixed with 8 parts of deionized water at 22° C. in a mixing vessel until a homogeneous mixture was obtained.

Compounding of Formulation of Example 1:

35 parts of Polyquaternium 44 were combined with 300 parts of deionized water in a mixing vessel until a homogeneous, clear mixture was obtained. While heating the clear mixture to a temperature of about 60° C. to about 71° C., 10 parts of PEG 150 distearate were added thereto with mixing until a homogeneous mixture was obtained. As the mixture was cooling to a temperature of 22° C., 10 parts of dimethicone copolyol and 5 parts of trimethylsilylamodimethicone were added thereto with stirring until the resulting mixture was clear.

The remaining surfactants were then added thereto with mixing: 55 parts of PEG-80 Sorbitan Laurate; 133 parts of cocamidopropyl betaine; 95 parts of sodium trideceth sulfate; and 28.5 parts of lauramphodiacetate. After 10 parts of glycerin were then added thereto with mixing, the resulting mixture was stirred until clear with a slight haze. 258 parts of water were then added thereto in order to cool the mixture to a temperature below 40° C.

After the mixture reached a temperature below 400 C, Preblends A through D followed by 1.8 parts of tetrasodium EDTA were added thereto consecutively with stirring. The pH was then checked and adjusted to about 5.9 to about 6.2 with additional citric acid solution. The amounts of the ingredients used to make the composition of Example 1 are shown in Table 1 below.

TABLE 1

Formulations of Conditioning Compositions

| Ingredient | CTFA Name | Source | % (w/w) Ex. 1A | % (w/w) Ex. 2 | % (w/w) Ex. 3 | % (w/w) Ex. 4 |
|---|---|---|---|---|---|---|
| DI-HOH | Water | | 57.760 | 57.760 | 57.760 | 57.760 |
| Luviquat Care | Polyquaternium 44 | BASF | 3.500 | 3.500 | 4.000 | 4.000 |
| Tegobetaine L7 | Cocamidopropyl Betaine | Goldschmidt | 13.300 | 13.300 | 13.300 | 13.300 |
| Cedepal TD-403 | Sodium Trideceth Sulfate | Stepan | 9.500 | 9.500 | 9.500 | 9.500 |
| Monateric 949J | Lauroamphodiacetate | Mona | 2.850 | 2.850 | 2.850 | 2.850 |
| Atlas G 4280 | PEG-80 Sorbitan Laurate | ICI Surfactants | 6.500 | 6.500 | 6.500 | 6.500 |
| PEG 6000 DS | PEG-150 Distearate | Stepan | 0.900 | 0.900 | 1.400 | 1.000 |
| Glycerin 916 | Glycerin | Henkel-Emery | 1.000 | 1.000 | 1.000 | 1.000 |
| Dowicil 200 | Quaternium - 15 | Dow Chemical | 0.050 | 0.050 | 0.050 | 0.050 |
| Versene 100 XL | Tetrasodium EDTA | Dow Chemical | 0.180 | 0.180 | 0.180 | 0.180 |
| Citrc Acid Anhydrous | Citric Acid | Roche Chemical | 0.200 | 0.200 | 0.200 | 0.200 |
| Fragrance | Fragrance | Givaudan | 0.350 | 0.350 | 0.350 | 0.350 |
| F D & C Red No.: 33 | F D & C Red No. 33 | Warner Jenkinson | 0.002 | 0.002 | 0.002 | 0.002 |
| Uvinul MS-40 | Benzophenone-4 | BASF | 0.150 | 0.150 | 0.150 | 0.150 |
| DI-HOH | Water | | 3.758 | 2.258 | 2.258 | 2.258 |
| DC Q2-8220 | Trimethylsilylamodimethicone | Dow Corning | 0.500 | — | 0.500 | 0.500 |
| DC 193 | Dimethicone Copolyol | Dow Corning | 1.000 | — | 1.000 | 0.500 |

Examples 2–4

Preparation of Conditioning Compositions

The procedure of Example 1 was repeated using the ingredients as set forth in Table 1 in order to make the conditioning compositions of Examples 2 through 4.

Example 5

Consumer Test of Conditioning Compositions

Samples of the compositions of Examples 1–4 were evaluated in consumer tests. In general, a test panel of 10 girls was given a blind sample of each respective formula tion in Table 1 as well as a blind sample of a commercial shampoo. The members were asked to use the samples in accordance with the procedure set forth above in the Half Head Study, and the results are provided in Table 2 below:

TABLE 2

Results of Half Head Study for Compositions of Examples 1 through 4

| Hair Attribute | Ex. 1 | Ex. 2 | Ex. 3 | Ex. 4 |
|---|---|---|---|---|
| Wet thickness (Means) | + | = | = | = |
| Wet Thickness (Frequency-top2) | −/= | + | −/= | + |
| Lather (means) | + | + | + | + |
| Lather (Frequency - top 2) | + | + | + | + |
| Rinsability (means) | = | − | + | − |
| Rinsability (Frequency - top 2) | = | − | − | −/= |
| Wet Detangling (means) | − | − | −(.4) | −(.56) |
| Wet Detangling (Frequency* - top 2) | − | − | − | −/= |
| Wet Feel (means) | − | = | − | = |
| Wet Feel (Frequency** - 3, 4) | + | = | −/= | −/= |
| Dry Combing (means) | − | + | − | + |
| Dry Combing (Frequency - top 2) | −/= | + | −/= | = |
| Dry softness (means) | + | − | − | + |
| Dry Softness (Frequency) | + | − | − | + |
| Dry Shine (means) | + | − | − | + |
| Dry Shine (Frequency - top 2) | + | −/= | − | + |
| Dry Body (means) | + | + | + | − |
| Dry Body (Frequency 3, 4) | − | + | − | + |
| Dry Static (means) | = | − | + | + |
| Dry Static (Frequency top 2) | = | − | − | + |
| Dry Feel (means) | + | + | + | − |
| Dry Feel (Frequency 3, 4) | + | + | = | + |

Symbols: +: perceived as superior to commercial product
−: commercial product perceived as superior
=: perceived as parity to commercial product
−/=: difference in frequency count of one between commercial product and experimental product
Frequency* (Top 2): refers to the comparison of the number of times a consumer evaluated a given property of an experimental formulation with a "4" or "5" rating with the number of times a consumer evaluated the same property of the commercial product with a "4" or "5" rating TABLE 2-continued Results of Half Head Study for Compositions of Examples 1 through 4

| Hair Attribute | Ex. 1 | Ex. 2 | Ex. 3 | Ex. 4 |
|---|---|---|---|---|

Frequency** (3, 4): refers to the comparison of the number of times a consumer evaluated a given property of an experimental formulation with a superior "3" or "4" rating with the number of times a consumer evaluated the same property of the commercial product with a superior "3" or "4" rating This Example showed that the formulation of Example 4, which contained a relative higher amount of Polyquaternium 44 in combination with the trimethylsilylamodimethicone and dimethicone copolyol silicone mixture in an equivalent weight ratio, imparted superior or comparable wet thickness, lather, rinsability, wet detangling, wet feel, dry combing, dry softness, dry shine, dry body, dry static, and dry feel properties relative to that imparted by the commercial shampoo.

This Example further illustrated that the compositions containing both Polyquaternium 44 and silicone conditioning agents were superior to a similar composition containing only Polyquaternium 44 with respect to wet thickness, rinsability, wet feel, dry softness, dry shine, and dry static.

Example 8

Wet Detangling Comb Force

Samples of both the shampoo compositions prepared in accordance with Examples 1–4 and the commercial NEW JOHNSON'S KIDS No More Tangles Shampoo were evaluated for wet detangling comb force in accordance with the procedure set forth above. The results of the evaluation, were obtained from tests on 7 tresses/formulation, are illustrated below in Table 3:

TABLE 3

Comparison of Wet Detangling Comb Force

| Formulation | MEDIAN FORCE (GMS) | DURATION SEC | MEDIAN STROKE ENERGY (G/SEC) | MEDIAN STROKE STROKES | CUM TIME | CUM ENERGY |
|---|---|---|---|---|---|---|
| Com'l MEAN*** | 160.57 | 0.92 | 134.34 | 7.14 | 6.41 | 1266.01 |
| Com'l STDEV | 19.10 | 0.19 | 34.19 | 0.38 | 0.63 | 273.19 |
| Ex. 1 MEAN* | 145.51 | 0.76 | 111.67 | 6.57 | 5.20 | 828.20 |
| Ex. 1 STDEV | 19.79 | 0.07 | 25.07 | 0.53 | 0.71 | 188.72 |
| Ex. 2 MEAN** | 178.31 | 1.02 | 195.34 | 7.29 | 8.96 | 1,449.59 |
| Ex. 2 STDEV | 39.76 | 0.22 | 62.04 | 0.76 | 6.32 | 338.35 |
| Ex. 3 MEAN* | 152.64 | 0.74 | 109.46 | 6.57 | 5.11 | 871.29 |
| Ex. 3 STDEV | 33.98 | 0.08 | 27.45 | 0.79 | 0.83 | 219.62 |
| Ex. 4 MEAN* | 160.64 | 0.78 | 115.40 | 6.71 | 5.16 | 927.50 |
| Ex. 4 STDEV | 33.31 | 0.06 | 21.19 | 0.76 | 0.66 | 190.73 |

*Ex. 1, 3, and 4 contain both a quaternary branched cationic polymer and a silicone conditioning agent
**Ex 2 contains only a quaternary branched cationic polymer conditioning agent
***Commercial shampoo contains a blend of cationic cellulosic polymer, guar gum and cyclomethicone conditioning agents These results further illustrated that the formulations of the present invention, which contain both a branched quaternary cationic polymer in combination with silicone polymers, demonstrated performance superior to shampoos containing both guar-based and cellulosic conditioning polymers along with silicones as well as to similar shampoos containing a single branched quaternary cationic polymer without a silicone conditioning agent. Thus, the combination of the branched quaternary cationic polymer along with the silicone polymers yielded synergistically superior results.

Examples 7 and 8

Preparation of Conditioning Compositions

The following pre-blends were prepared.

Preblend A:

1.5 parts of benzophenone 4 were mixed with 3 parts deionized water at 22° C. in a mixing vessel until a homogeneous mixture was obtained.

Preblend B:

0.1 part of dye was mixed with 10 parts of deionized water at 22° C. in a mixing vessel until a homogeneous mixture was obtained.

Preblend C:

3.5 parts of fragrance were mixed with 10 parts of PEG-80 sorbitan laurate at 22° C. in a mixing vessel until a homogeneous mixture was obtained.

Preblend D:

0.5 parts of Quaternium 15 were mixed with 1 part of deionized water at 22° C. in a mixing vessel until a homogeneous mixture was obtained.

Preblend E:

2 parts of citric acid were mixed with 8 parts of deionized water at 22° C. in a mixing vessel until a homogeneous mixture was obtained.

Compounding of Formulation of Examples 7 and 8:

3.2 parts of Polyquaternium 10 were combined with 300 parts of deionized water in a mixing vessel until a homogeneous, mixture was obtained with no floating particles present. While heating the mixture to a temperature of about 60° C. to about 71° C., 5 parts of PEG 150 distearate were added thereto with mixing until a homogeneous mixture was obtained. As the mixture was cooling to a temperature of 22° C., the remaining ingredients were added with stirring in between each addition until the resulting mixture was homogeneous: 55 parts of PEG-80 Sorbitan Laurate; 133 parts of cocamidopropyl betaine; 5 parts of dimethicone copolyol; 28.5 parts of lauramphodiacetate and 95 parts of sodium trideceth sultate;. After 10 parts of glycerin were then added thereto with mixing, the resulting mixture was stirred until clear with a slight haze. The remaining parts of water were then added thereto in order to cool the mixture to a temperature below 40° C.

After the mixture reached a temperature below 40° C., Preblends A through D followed by 1.8 parts of tetrasodium EDTA and 5 parts of trimethylsilylamodimethicone were added thereto consecutively with stirring. The batch was mixed for a final 7 minutes until homogeneous. The pH was then checked and adjusted to about 5.8 to about 6.2 with additional citric acid solution.

This Example was repeated but the Polyquaternium 10 was replaced with an equivalent amount of guar hydroxypropyltrimonium chloride.

The amounts of the ingredients used to make the composition of Examples 9 and 10 are shown in Table 4 below.

TABLE 4

Formulations of Compositions of Example 7 and Example 8

| Ingredient | CTFA Name | Source | % (w/w) Ex. 7 | % (w/w) Ex. 8 |
|---|---|---|---|---|
| DI-HOH | Water | | 64.098 | 64.098 |
| Ucare Polymer JR400 | Polyquaternium 10 | Amerchol | 0.32 | — |
| Jaguar C17 | Guar Hydroxypropyltrimonium Chloride | Rhone Poulenc | — | 0.32 |
| Tegobetaine L7 | Cocamidopropyl Betaine | Goldschmidt | 13.300 | 13.300 |
| Cedepal TD-403 | Sodium Trideceth Sulfate | Stepan | 9.500 | 9.500 |
| Monateric 949J | Lauramphodiacetate | Mona | 2.850 | 2.850 |
| Atlas G 4280 | PEG-80 Sorbitan Laurate | ICI Surfactants | 6.500 | 6.500 |
| PEG 6000 DS | PEG-150 Distearate | ICI | 0.500 | 0.500 |
| Glycerin 916 | Glycerin | Henkel-Emery | 1.000 | 1.000 |
| Dowicil 200 | Quaternium - 15 | Dow Chemical | 0.050 | 0.050 |
| Versene 100 XL | Tetrasodium EDTA | Dow Chemical | 0.180 | 0.180 |
| Citrc Acid Anhydrous | Citric Acid | Roche Chemical | 0.200 | 0.200 |
| Fragrance | Fragrance | Givaudan | 0.350 | 0.350 |
| F D & C Blue No. 1 | F D & C Blue No. 1 | Warner Jenkinson | 0.002 | 0.002 |
| Uvinul MS-40 | Benzophenone-4 | BASF | 0.150 | 0.150 |
| DC Q2-8220 | Trimethylsilylamodimethicone | Dow Corning | 0.500 | 0.500 |
| DC 193 | Dimethicone Copolyol | Dow Corning | 0.500 | 0.500 |

Example 9

Preparation of Conditioning Composition

The following pre-blends were prepared.

Preblend A:

1.5 parts of benzophenone 4 were mixed with 3 parts deionized water at 22° C. in a mixing vessel until a homogeneous mixture was obtained.

Preblend B:

0.1 part of dye was mixed with 10 parts of deionized water at 22° C. in a mixing vessel until a homogeneous mixture was obtained.

Preblend C:

3.5 parts of fragrance were mixed with 10 parts of PEG-80 sorbitan laurate at 22° C. in a mixing vessel until a homogeneous mixture was obtained.

Preblend D:

0.5 parts of Quaternium 15 were mixed with 1 part of deionized water at 22° C. in a mixing vessel until a homogeneous mixture was obtained.

Preblend E:

2 parts of citric acid were mixed with 8 parts of deionized water at 22° C. in a mixing vessel until a homogeneous mixture was obtained.

Compounding of Formulation of Example 9:

40 parts of Polyquaternium 44 were combined with 300 parts of deionized water in a mixing vessel until a homogeneous, mixture was obtained with no floating particles present. While heating the mixture to a temperature of about 60° C. to about 71° C., 9 parts of PEG 150 distearate were added thereto with mixing until a homogeneous mixture was obtained. As the mixture was cooling to a temperature of 22° C., the remaining ingredients were added thereto with stirring in between the addition of each ingredient until each intermediate resulting mixture was homogeneous: 27.5 parts of PEG-80 Sorbitan Laurate; 3.75 parts of dimethicone copolyol; 28.5 parts of lauramphodiacetate; 10 parts of glycerin; 66.5 parts of cocamidopropyl betaine; 27.5 parts of PEG-80 Sorbitan Laurate; 47.5 parts of sodium trideceth sulfate. After the remaining water, 66.5 parts of cocamidopropyl betaine and 47.5 parts of sodium trideceth sulfate were added there to in order to cool the mixture, the resulting mixture was stirred until clear to slightly hazy.

After the mixture reached a temperature below 40° C., Preblends A through D followed by 1.8 parts of tetrasodium EDTA and 10 parts of dimethicone copolyol were added thereto consecutively with stirring. The batch was mixed for a final 7 minutes until homogeneous. The pH was then checked and adjusted to about 6.9–7.2 with additional citric acid solution. The amounts of the ingredients used to make the composition of Example 9 are shown in Table 5 below.

TABLE 5

Formulations of Conditioning Composition

| Ingredient | CTFA Name | Source | % (w/w) Ex. 9A |
|---|---|---|---|
| DI-HOH | Water | | 57.760 |
| Luviquat Care | Polyquaternium 44 | BASF | 4.0 |
| Tegobetaine L7 | Cocamidopropyl Betaine | Goldschmidt | 13.300 |
| Cedepal TD-403 | Sodium Trideceth Sulfate | Stepan | 9.500 |
| Monateric 949J | Lauramphodiacetate | Mona | 2.850 |
| Atlas G 4280 | PEG-80 Sorbitan Laurate | ICI Surfactants | 6.500 |
| PEG 6000 DS | PEG-150 Distearate | Stepan | 0.900 |
| Glycerin 916 | Glycerin | Henkel– | 1.000 |

TABLE 5-continued

Formulations of Conditioning Composition

| Ingredient | CTFA Name | Source | % (w/w) Ex. 9A |
|---|---|---|---|
| Dowicil 200 | Quaternium - 15 | Emery Dow Chemical | 0.050 |
| Versene 100 XL | Tetrasodium EDTA | Dow Chemical | 0.180 |
| Citrc Acid Anhydrous | Citric Acid | Roche Chemical | 0.200 |
| Fragrance | Fragrance | Givaudan | 0.350 |
| F D & C Red No.: 33 | F D & C Red No. 33 | Warner Jenkinson | 0.002 |
| Uvinul MS-40 | Benzophenone-4 | BASF | 0.150 |
| DI-HOH | Water | | 3.758 |
| DC 5324 | Dimethicone Copolyol | Dow Corning | 1.000 |
| DC 193 | Dimethicone Copolyol | Dow Corning | 0.375 |

Example 10

Wet Detangling Comb Force

Samples of both the shampoo compositions prepared in accordance with Examples 7 and 8, and the shampoo prepared in accordance with Example 9 (containing Polyquaternium 44 and Dimethicone Copolyol) were evaluated for wet detangling comb force in accordance with the procedure set forth above. The results of the evaluation, were obtained from tests on 7 tresses/formulation, are illustrated below in Table 6:

TABLE 6

Comparison of Wet Detangling Comb Force

| Formulation | MEDIAN FORCE (GMS) | DURATION SEC | MEDIAN STROKE ENERGY (G/SEC) | STROKES | CUM TIME | CUM ENERGY |
|---|---|---|---|---|---|---|
| Ex. 7 MEAN* Comparative | 137.53 | 0.83 | 107.54 | 6.43 | 5.24 | 755.40 |
| Ex. 7 STDEV | 25.53 | 0.10 | 17.05 | 1.13 | 0.83 | 143.91 |
| Ex. 8 MEAN** Comparative | 153.11 | 1.04 | 149.23 | 6.86 | 6.69 | 1229.21 |
| Ex. 8 STDEV | 35.64 | 0.08 | 40.07 | 0.69 | 0.35 | 175.09 |
| Ex. 9 MEAN*** | 109.14 | 0.76 | 87.43 | 6.43 | 5.13 | 669.93 |
| Ex. 9 STDEV | 23.58 | 0.11 | 27.64 | 0.79 | 0.60 | 80.51 |

*Ex. 7 contains Polyquaternium 10 along with a combination of a trimethylsilylamodimethicone and dimethicone copolyol silicone mixture
**Ex 8 contains guar hydroxypropyltrimonium chloride along with a combination of a trimethylsilylamodimethicone and dimethicone copolyol silicone mixture;
***Ex. 9 contains Polyquaternium 44 along with a combination of a dual dimethicone copolyol silicone mixture.

These results further illustrated that the formulations of the present invention, which contain both a branched quaternary cationic polymer in combination with silicone polymers, demonstrated superior wet detangling performance relative to shampoos containing a guar-based conditioning polymer in combination with silicone polymers as well as to shampoos containing a cellulosic conditioning polymer in combination with silicone polymers. Thus, this Example further showed that the unique combination of the branched quaternary cationic polymer along with the silicone polymers yielded synergistically superior results.

Example 11

Conditioning Shampoo

A conditioning shampoo was prepared in accordance with Example 9. The amounts of the ingredients used to make the composition of Example 11 are shown in Table 7 below:

TABLE 7

Formulations of Composition of Example 11

| Ingredient | CTFA Name | Source | % (w/w) Ex. 9A |
|---|---|---|---|
| DI-HOH | Water | | q.s. |
| Luviquat Care | Polyquaternium 44 | BASF | 3.5 |
| Tegobetaine L7 | Cocamidopropyl Betaine | Goldschmidt | 13.3 |
| Cedepal TD-403 | Sodium Trideceth Sulfate | Stepan | 9.0 |
| Plantaren 2000 | Decyl Glucoside | Henkel | 2.8 |
| Atlas G 4280 | PEG-80 Sorbitan Laurate | ICI Surfactants | 1.0 |
| PEG 6000 DS | PEG-150 Distearate | Stepan | 1.7 |
| Glycerin 916 | Glycerin | Henkel–Emery | 1.0 |
| Dowicil 200 | Quaternium - 15 | Dow Chemical | 0.050 |
| Versene 100 XL | Tetrasodium EDTA | Dow Chemical | 0.26 |
| Citrc Acid Anhydrous | Citric Acid | Roche Chemical | 0.08 |
| Fragrance | Fragrance | Givaudan | 0.5 |
| Dye | | | 0.002 |
| Uvinul MS-40 | Benzophenone-4 | BASF | 0.2 |
| DC 5324 | Dimethicone Copolyol | Dow Corning | 0.75 |
| DC 193 | Dimethicone Copolyol | Dow Corning | 0.375 |

Example 12

TEP—Eye Irritation

The potential for eye irritation of the conditioning shampoos of Examples 9 and 11 were measured by the TEP test as described above. The results are set forth in Table 8 below:

TABLE 8

| | TEP Test | |
|---|---|---|
| Sample | MEAN $EC_{50}$ + δn-1 | RATING |
| Example 9 | 4.39 +/− 0.68 | Pass |
| Example 11 | 4.39 +/− 0.68 | Pass |

The results above suggest that the compositions of this invention are not irritating to human eyes. This was confirmed in the following human ocular irritation test.

Example 13

Human Ocular Irritation Test

The samples from Example 9 and 11 were also tested in the human ocular irritation test described above. The test was performed on ten people. For both samples, only one person initially felt a mild stinging sensation which disappeared within 15 minutes. The other nine people for each sample did not feel a stinging sensation. The results of the tests demonstrated the compositions of this invention produce only mild and transient ocular stinging, at levels which did not differ from sterile water.

We claim:
1. A conditioning composition comprising:
   from about 5 percent to about 20 percent, based upon the total weight of said conditioning composition of a surfactant portion comprising:
   1. a nonionic surfactant;
   2. an amphoteric surfactant; and
   3. an anionic surfactant; and
   from about 0.1 percent to about 6.0 percent, based upon th total weight of the conditioning composition of a conditioner portion comprising:
   1. at least one vinylpyrrolidoine/vinylimidazolium copolymer; and
   2. a non-volitale silicone selected from the group consisting of cetyl dimethicone; cetyl triethylammonium dimethicone copolyol phthalate; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; phenyl trimethicone; amodimethicones; polyalkylarylsiloxanes; and mixtures thereof; wherein th weight ratio of branched quaternary cationic polymer to silicone ranges from about 1:4 to aout 1:6.

2. The conditioning composition of claim 1 wherein the conditioner portion is present in an amount, based upon the total weight of the detergent composition, from about 0.5 percent to about 4.0 percent.

3. The conditioning composition of claim 1 comprised of, based upon the total weight of the conditioning composition, from about 5 percent to about 20 percent of the surfactant portion and from about 1.0 percent to about 3.0 percent of the conditioning portion.

4. The conditioning composition of claim 1 comprised of, based upon the total weight of the conditioning composition, from about 5 percent to about 15 percent of the surfactant portion and from about 1.0 percent to a out 3.0 percent of the conditioning portion.

5. The conditioning composition of claim 1 comprised of, based upon the total weight of the conditioning composition, from about 0.001 percent to about 5.0 percent of the at least one vinylpyrrolidoine/vinylimidazolium copolymer.

6. The conditioning composition of claim 1 comprised of, based upon the total weight of the conditioning composition, from about 0.01 percent to about 3.0 percent of the at least one vinylpyrrolidoine/vinylimidazolium copolymer.

7. The conditioning composition of claim 1 comprised of, based upon the total weight of the conditioning composition, from about 0.01 percent to about 8.0 percent of the non-volatile silicone.

8. The conditioning composition of claim 1 comprised of, based upon the total weight of the conditioning composition, from about 0.1 percent to about 5.0 percent of the non-volatile silicone.

9. The conditioning composition of claim 1 comprised of, based upon the total weight of the conditioning portion, from about 6 percent to about 25 percent of the at least one vinylpyrrolidoine/vinylimidazolium copolymer.

10. The conditioning composition of claim 1 comprising, based upon the total weight of the conditioning portion, from about 10 percent to about 22 percent of said at least one vinylpyrrolidoine/vinylimidazolium copolymer.

11. The conditioning composition of claim 1 wherein the at least one vinylpyrrolidoine/vinylimidazolium copolymer is selected from the group consisting of polyquaternium 44, polyquaternium 16, and mixtures thereof.

12. The conditioning composition of claim 1 wherein said at least one vinylpyrrolidoine/vinylimidazolium copolymer is a mixture of, based upon the total weight of vinylpyrrolidoine/vinylimidazolium copolymer, from about 70 percent to about 90 percent of polyquaternium 44 and from about 30 percent to about 10 percent polyquaternium 16.

13. The conditioning composition of claim 1 wherein the non-volatile silicone is a non-volatile silicone having a viscosity of from about 10 to about 5000 centistokes at 25° C.

14. The conditioning composition of claim 1 wherein the at least one vinylpyrrolidoine/vinylimidazolium copolymer has a cationic charge density of about 1.0 meq/gram about 6.5 meq/gram.

15. The detergent composition of claim 1 wherein the nonionic surfactant selected from the group consisting of
   a) a polyoxyethylene derivative of a polyol ester
      1. derived from a fatty acid, from 8 to 22 carbon atoms and a polyol selected from sorbitol, sorbitan, glucose, α-methyl glucoside, polyglucose having an average of about to about 1 to about 3 glucose residues, glycerine, pentaerythritol and mixtures thereof,
      2. containing an average of 10 to 120 oxyethylene units, and
      3. having an average of from 1 to 3 fatty acid residues per molecule of the polyoxyethylene derivative of polyol ester,
   b) an alkyl glucoside having an alkyl group from 6 to 22 carbon atoms and having from 1 to 6 glucose residues per molecule of alkyl glucoside, or
   c) mixtures thereof,
wherein the nonionic surfactant is present in an amount, based upon the total weight of the detergent composition, of from about 0.1 percent to about 10 percent.

16. The detergent composition of claim 1 wherein the amphoteric surfactant is selected from the group consisting of:
   a. an amphocarboxylate compound of the formula:

wherein
      A is an alkyl or alkenyl group having 7 to 21 carbon atoms;
      x is an integer of from 2 to 6;
      $R_5$ is hydrogen or a carboxyalkyl group from 2 to 3 carbon atoms;
      $R_6$ is a hydroxyalkyl group from 2 to 3 carbon atoms or is a group of the formula:

$R_8$—O—$(CH_2)_n CO_2$ wherein
         $R_8$ is an alkylene group having from 2 to 3 carbon atoms and
         n is 1 or 2; and
      $R_7$ is a carboxyalkyl group from 2 to 3 carbon atoms;
   b. an alkyl betaine of the formula:

wherein
      B is an alkyl or alkenyl group having from 8 to 22 carbon atoms;
      $R_9$ and $R_{10}$ are each independently an alkyl group or a hydroxyalkyl group having from 1 to 4 carbon atoms, and
      p is 1 or 2;
   c. an amidoalkyl betaine of the formula:

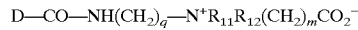

wherein
      D is an alkyl or alkenyl group having from 7 to 21 carbon atoms;
      $R_{11}$ and $R_{12}$ are each independently an alkyl or a hydroxyalkyl group having from 1 to 4 carbon atoms;
      q is an integer from 2to 6; and
      m is 1 or 2;
   d. an amidoalkyl sultaine of the formula:

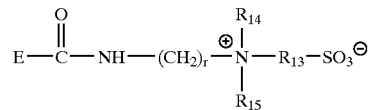

wherein
      E is an alkyl group or alkenyl group having from 7 to 21 carbon atoms;
      $R_{14}$ and $R_{15}$ are each independently an alkyl group or a hydroxyalkyl group having from 1 to 4 carbon atoms;
      r is an integer from 2 to 6; and
      $R_{13}$ is an alkylene or hydroxyalkylene group having from about 2 to 3 carbon atoms;
   e. an amphophosphate compound of formula:

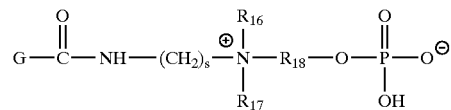

wherein
      G is an alkyl group or alkenyl group having 7 to 21 carbon atoms;
      s is an integer from 2 to 6;
      $R_{16}$ is hydrogen or a carboxyalkyl group from 2 to 3 carbon atoms;
      $R_{17}$ is a hydroxyalkyl group from 2 to 3 carbon atoms or is a group of the formula:

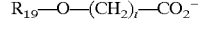

wherein
         $R_{19}$ is an alkylene group having from 2 to 3 carbon atoms and
         t is 1 or 2; and
      $R_{18}$ is an alkylene or hydroxyalkylene group having from 2to 3 carbon atoms;
   f. a phosphobetaine compound of formula:

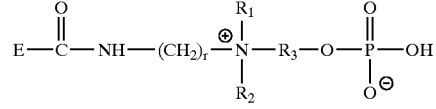

wherein E, r, $R_1$, $R_2$, $R_3$, are as defined above;

g. a pyrophosphobetaine compound of formula:

$$E-\overset{O}{\overset{\|}{C}}-NH-(CH_2)_r-\overset{R_1}{\underset{R_2}{\overset{\oplus}{N}}}-R_3-O-\overset{O}{\underset{O^\ominus}{\overset{\|}{P}}}-O-\overset{O}{\underset{O^\ominus}{\overset{\|}{P}}}-OH$$

wherein E, r, $R_1$, $R_2$, $R_3$, are as defined above:

h. a carboxyalkyl alkylpolyamine of formula:

$$I-\left[\underset{R_{22}}{\overset{}{N}}-R_{21}\right]_u-N\underset{R_{22}}{\overset{R_{22}}{\diagdown}}$$

wherein
I is an alkyl or alkenyl group from 8 to 22 carbon atoms,
$R_{22}$ is a carboxyalkyl group having from to 2 to 3 carbon atoms;
$R_{21}$ is an alkylene group having from 2 to 3 carbon atoms and
u is an integer from 1 to 4; and i,) mixtures thereof, wherein the amphoteric surfactant is present in an amount, based upon the total weight of the detergent composition, of from about 0.5 percent to about 10 percent.

17. The detergent composition of claim 16 wherein $R_5$ is hydrogen.

18. The detergent composition of claim 10 wherein the amphoteric surfactant comprises, based upon the total weight of the detergent composition, from about 0.5 percent to about 9.5 percent of an alkyl betanine, amidoalkyl betaine, or mixtures thereof, the alkyl group having from 8 to 22 carbon atoms; and about 0.5 percent to about 9.5 percent of an amphocarboxylate.

19. The detergent composition of claim 1 wherein the anionic surfactant is selected from the group consisting of:

an alkyl sulfate of the formula:

$R'-CH_2OSO_3X'$;

an alkyl ether sulfate of the formula:

$R'(OCH_2CH_2)_vOSO_3X'$;

an alkyl monoglyceryl ether sulfate of the formula:

$R'OCH_2CHCH_2OSO_3X'$;
    |
    OH an alkyl monoglyceride sulfate of the formula:

$R'CO_2CH_2CHCH_2OSO_3X'$;
       |
       OH an alkyl monoglyceride sulfonate of the formula:

$R'CO_2CH_2CHCH_2SO_3X'$;
       |
       OH an alkyl sulfonate of the formula:

$R'-SO_3X'$;

an alkylaryl sulfonate of the formula:

$R'_1-\phantom{}\bigcirc\phantom{}-SO_3X'$;

an alkyl sulfosuccinate of the formula:

$R'O_2C\diagdown\diagup CO_2X'$;
         |
         $SO_3X'$ an alkyl ether sulfosuccinate of the formula:

$R'-(OCH_2CH_2)_v-O_2C\diagdown\diagup CO_2X'$;
                         |
                         $SO_3X'$ an alkyl sulfosuccinamate of the formula:

$R'-\underset{H}{N}-\overset{O}{\overset{\|}{C}}\diagdown\diagup CO_2X'$;
                         |
                         $SO_3X'$ an alkyl amidosulfosuccinate of the formula:

$R'-\overset{O}{\overset{\|}{C}}-NH-CH_2CH_2-(OCH_2CH_2)_w-O_2C\diagdown\diagup CO_2X'$;
                                                           |
                                                           $SO_3X'$ an alkyl carboxylate of the formula:

$R'-(OCH_2CH_2)_w-OCH_2CO_2X'$;

an alkyl amidoethercarboxylate of the formula:

$R'-\overset{O}{\overset{\|}{C}}-NH-CH_2CH_2-(OCH_2CH_2)_w-OCH_2CO_2X'$;

an alkyl succinate of the formula:

$R'\diagdown_O\diagup\overset{O}{\overset{\|}{C}}\diagdown\diagup CO_2X'$;

a fatty acyl sarcosinate of the formula:

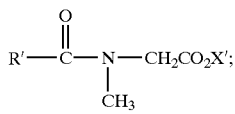

a fatty acyl amino acid of the formula:

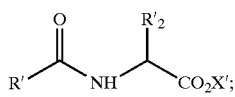

a fatty acyl taurate of the formula:

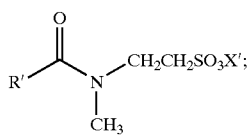

a fatty alkyl sulfoacetate of the formula:

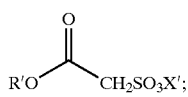

an alkyl phosphate of the formula:

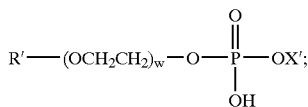

and mixtures thereof
wherein
R' is an alkyl group having from 7 to 22 carbon atoms,
$R'_1$ is an alkyl group having from 1 to 18 carbon atoms,
$R'_2$ is a substituent of a natural or synthetic α-amino acid,
X' is selected from the group consisting of alkali metal ions, alkaline earth metal ions, ammonium ions, and ammonium ions substituted with 1 to 3 substituents, each of the substituents may be the same or different and are selected from alkyl groups having from 1 to 4 carbon atoms and hydroxyalkyl groups having from 2 to 4 carbon atoms and
v is an integer from 1 to 6;
w is an integer from 0 to 20;
wherein the anionic surfactant is present in an amount, based upon the total weight of the shampoo composition of from about 1 percent to about 10 percent.

20. A conditioning detergent composition comprising, based upon the total weight of the detergent composition:

a. from about 1 percent to about 10 percent of nonionic surfactants selected from the group consisting of:
1) a polyoxyethylene derivative of a polyol ester
   a. derived from a fatty acid from 8 to 22 carbon atoms and a polyol select from sorbitol, sorbitan, glucose, α-methyl glucoside, polyglucose having an average of 1 to 3 glucose residues, glycerine, pentaerythritol and mixtures thereof,
   b. containing an average of from 10 to 120 oxyethylene units, and
   c. having an average of from 1 to 3 fatty acid residues per molecule of the polyoxyethylene derivative of polyol ester,
2) an alkyl glucoside having an alkyl group from 6 to 22 carbon atoms and having from 1 to 6 glucose residues per molecule of alkyl glucoside, or
3) mixtures thereof, and b. from about 0.5 percent to about 10 percent of one or more amphocarboxylate amphoteric surfactants of the formula:

wherein
A is an alkyl or alkenyl group having from 7 to 21 carbon atoms;
x is an integer of from 2 to 6;
$R_5$ is hydrogen or a carboxyalkyl group from 2 to 3 carbon atoms;
$R_6$ is a hydroxyalkyl group from 2 to 3 carbon atoms or a group of the formula:

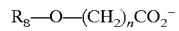

wherein
$R_8$ is an alkylene group having from 2 to 3 carbon atoms and
n is 1 or 2; and
$R_7$ is a carboxyalkyl group from 2 to 3 carbon atoms, c. from about 0.5 percent to about 10 percent of one or more betaine amphoteric surfactants selected from:
1) an alkyl betaine of the formula:

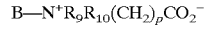

wherein
B is an alkyl or alkenyl group having from 8 to 22 carbon atoms;
$R_9$ and $R_{10}$ are each independently an alkyl group or a hydroxyalkyl group having from 1 to 4 carbon atoms; and
p is 1 or 2; or
2) an amidoalkyl betaine of the formula:

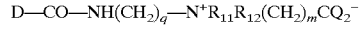

wherein
D is an alkyl or alkenyl group having from 7 to 21 carbon atoms;
$R_{11}$ and $R_{12}$ are each independently an alkyl group or a hydroxyalkyl group having from 1 to 4 carbon atoms;
q is an integer from 2 to 6; and
m is 1 or 2;

d. from about 1 percent to about 10 percent of one or more anionic alkyl ether sulfate surfactants of the formula:

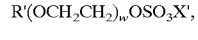

wherein
R' is an alkyl or alkenyl group having from 7 to 22 carbon atoms,
X' is selected from the group consisting of alkali metal ions, alkaline earth metal ions, ammonium ions, ammonium ion substituted with from 1 to 3 substituents, each of the substituents may be the same or different and are selected from alkyl groups having from 1 to 4 carbon atoms and hydroxyalkyl groups having from 2 to 4 carbon atoms, and v is an integer from 1 to 6;

e. from about 0.001 percent to about 5.0 percent of polyquaternium 44; and f. from about 0.01 percent to about 8.0 percent of silicone;

wherein the surfactants in a through d are present in an amount, based upon the total weight of the detergent composition, from about 5 percent to about 20 percent.

21. The detergent composition of claim 20 further comprising from about 0.5 percent to about 5 percent, based upon the total weight of the detergent composition, of a humectant comprising glycerine.

22. A conditioning detergent composition comprising, based upon the total weight of the detergent composition:

a. from about 2 percent to about 10 percent of a polyoxyethylene derivative of polyol ester nonionic surfactant derived from
   1) a polyol comprised of sorbitol, sorbitan, and mixtures thereof, and
   2) lauric acid,
   containing an average of from about 20 to about 80 oxyethylene units per molecule of a polyoxyethylene derivative of polyol ester, and
   having an average of from about 1 to about 2 lauric acid residues per molecule of a polyoxyethylene derivative of polyol ester, and mixtures thereof;

b. from about 0.5 percent to about 5 percent of an amphocarboxylate amphoteric surfactant of the formula:

   A—CONH(CH$_2$)$_x$N$^+$R$_5$R$_6$R$_7$ wherein
   A is an alkyl group having 11 carbon at atoms,
   x is 2,
   R$_1$ is hydrogen,
   R$_5$ is a group of the formula R$_8$—O—(CH$_2$)$_n$CO$_2^-$ wherein
   R$_8$ is a 2 carbon alkylene group; and
   n is 1; and
   R$_7$ is a carboxymethyl group, and mixtures thereof;

c. from about 0.5 percent to about 8 percent of a betaine surfactant selected from:
   1) an alkyl betaine of the formula:

B—N$^+$R$_9$R$_{10}$CH$_2$CO$_2^-$ wherein B is a lauryl group having 12 carbon atoms, and
   R$_1$ and R$_2$ are each methyl groups,
   2) an amidoalkyl betaine of the formula:

D—CO—NH(CH$_2$)$_q$—N$^+$R$_{11}$R$_{12}$CH$_2$CO$_2^-$ wherein
   DCO represents a fatty acid derived from coconut oil,
   q is 3 and
   R$_{11}$, and R$_{12}$ are each methyl groups, and
   3) mixtures thereof;

d. from about 2 percent to about 8 percent of an alkyl ether sulfate anionic surfactant of the formula:

R'(OCH$_2$CH$_2$)$_v$OSO$_3$X', wherein
   R' is an alkyl group having from 12 to 13 carbon atoms,
   X is a sodium ion; and
   v is an integer from 1 to 4, and mixtures thereof;

e. from about 0.001 percent to about 5.0 percent of Polyquaternium-44;

f. from about 0.01 percent to about 8.0 percent of trimethylsilylamodimethicone, dimethicone copolyol, or mixtures thereof;

wherein the surfactants a through d are present in an amount, based upon the total weight of the detergent composition, of from about 5 percent to about 20 percent.

23. The composition of claim 1 in the form of a shampoo, a conditioner, a body wash, a shower gel, or a bath wash.

* * * * *